United States Patent [19]

Gilman

[11] Patent Number: 4,979,946
[45] Date of Patent: Dec. 25, 1990

[54] ENVIRONMENTAL ABSORBENT DRESSING

[75] Inventor: Thomas Gilman, Mansfield, Mass.

[73] Assignee: The Kendall Company, Boston, Mass.

[21] Appl. No.: 335,072

[22] Filed: Apr. 7, 1989

Related U.S. Application Data

[63] Continuation-in-part of Ser. No. 132,436, Dec. 14, 1987, abandoned.

[51] Int. Cl.[5] .................... A61F 13/02; A61F 13/00
[52] U.S. Cl. .................................. 604/307; 128/156; 604/368; 424/448
[58] Field of Search ............... 128/155, 156; 604/304, 604/307, 370, 375, 372, 364, 378, 383, 360, 368; 5/485, 502; 523/111; 424/445, 447, 448

[56] References Cited

U.S. PATENT DOCUMENTS

| 3,598,122 | 8/1971 | Zaffaroni. | |
| 4,379,454 | 4/1983 | Campbell et al. | 604/897 |
| 4,516,571 | 5/1985 | Buchan | 128/132 R |
| 4,541,426 | 9/1985 | Webster | 128/156 |
| 4,542,012 | 9/1985 | Dell | 424/48 |
| 4,657,006 | 4/1987 | Rawlings et al. | 128/156 |
| 4,759,354 | 7/1988 | Quarfoot | 128/156 |
| 4,909,244 | 3/1990 | Quarfoot et al. | 128/156 |

Primary Examiner—Randall L. Green
Assistant Examiner—Paul Prebilic
Attorney, Agent, or Firm—Alvin Isaacs

[57] ABSTRACT

An environmental absorbent dressing having, an absorbent layer comprising a hydrogel, and a front sheet comprising a film capable of permitting passage of liquid covering a front surface of the absorbent layer and coated on a front surface thereof with a porous adhesive.

12 Claims, 1 Drawing Sheet

ENVIRONMENTAL ABSORBENT DRESSING

CROSS REFERENCE TO RELATED APPLICATION

The present application is a continuation-in-part of Ser. No. 132,436, filed Dec. 14, 1987 now abandoned.

This application is related to Ser. No. 935,426, filed Nov. 26, 1986, now U.S. Pat. No. 4,909,244.

BACKGROUND OF THE INVENTION

The present invention relates to absorbent dressings.

It has been shown that it is advantageous to maintain a moist environment at the surface of a wound, with the advantages including faster healing, less pain, and rapid material debridement of the wound.

It is not advantageous to have fluid from the wound come in contact with the skin surrounding the wound. Disadvantages of such a result are maceration, irritation and multipication of skin organisms and their migration into the wound bed.

A goal of a good dressing design, then, is to maintain a moist environment of the wound surface while removing excess fluid from contacting the skin surrounding the wound.

A manner in which to protect the skin around the wound is to provide an adhesive seal up to the wound margin. Many dressings that provide this seal, however, do not provide the ability to handle wound fluid well enough to keep the seal from being undermined by fluid produced in the wound. In addition, sweat produced by sweat glands in the skin will undermine typical pressure sensitive adhesive.

A material which has proven to have a capacity that is sufficient to absorb fluid in the amounts produced by a wound is a hydrogel. When this hydrogel is used to dress a wound, fluid is effectively kept from the skin surrounding the wound. However, when the hydrogel is in direct contact with the wound, it retards healing of the wound.

SUMMARY OF THE INVENTION

A principal feature of the present invention is the provision of an improved absorbent dressing.

The absorbent dressing of the present invention comprises, an absorbent layer comprising a hydrogel, and a front sheet comprising a film covering a front surface of the absorbent layer coated on a front surface thereof with a porous adhesive.

A feature of the present invention is that the front sheet shields the wound from the absorbent layer.

A further feature of the invention is that the front sheet carries on the free outer (front) surface an adhesive layer for securing the dressing to the skin, the front sheet being of a nature (to be described in more detail hereinafter) to provide a unitary dressing of the requisite structural integrity having both an absorbent layer and an adhesive layer for applying the dressing.

Another feature of the invention is that the front sheet is capable of permitting passage of liquid therethrough to the absorbent layer.

Still another feature of the invention is that fluids transferred through the front sheet into the absorbent layer are effectively kept from the surrounding skin.

Yet another feature of the invention is that the wound surface is maintained in a moist condition such that healing is rapid.

Further features will become more fully apparent in the following description of the embodiments of this invention and from the appended claims.

DESCRIPTION OF THE PREFERRED EMBODIMENTS

Figure 1:
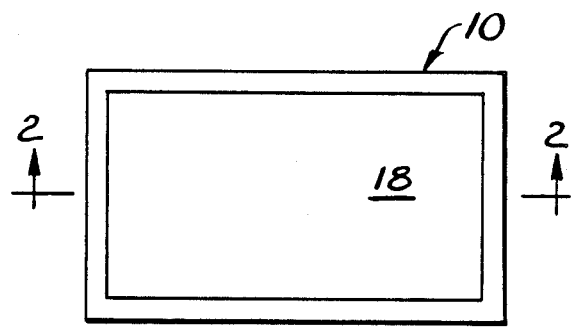
Fig 1 is A top plan view of a dressing of the present invention.
Figure 2:
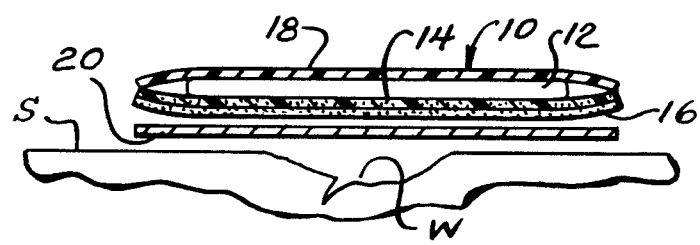
FIG. 2 is a sectional view taken substantially as indicated along the line 2—2 of FIG. 1.

Referring now to FIGS. 1 and 2, there is shown an absorbent dressing generally designated 10 of the present invention. The dressing 10 has an absorbent layer 12 comprising a hydrogel, e.g. the acrylic based hydrogel commercially available from Medtronics Inc. under the trademark "EnerTac" NDO, designated NDO, a material which swells in water but dissolved by water. The hydrogel of the absorbent layer 12 absorbs at least 200% of its original weight in water.

The dressing has a front sheet or film 14 covering a front surface of the absorbent layer 12, and shielding the absorbent layer 12 from a wound W. The front sheet 14 has a porous adhesive 16 covering a front surface of the front sheet 14 which permits passage of fluid from the wound, including water transport, to the front sheet 14 where fluids are transferred by the front sheet 14 into the absorbent layer 12 in order to keep the fluids from the surrounding skin. In this manner, the fluids are effectively kept from the surrounding skin, and the wound surface is maintained in a moist condition, such that healing of the wound is rapid.

An important feature of this invention resides in the fact that it is exceedingly difficult, if not impossible, to adhere the adhesive layer necessary for applying the dressing directly to the hydrogel layer so as to obtain an integral or unitary product having the requisite structural integrity for its contemplated use as a wound dressing.

In accordance with this invention, this task may be accomplished by employing for front film 14 a water-swellable, water-insoluble polymer that is characterized as being elastomeric when dry. A film of this description may be readily laminated in the dry state to adhesive layer 16, e.g. by heat-sealing.

Suitable polymers of this description are the class of per se known block polymers having hard segments, e.g. nylon, polyester, polyurethane, polystyrene or polycarbonate, which are glass or crystalline at room temperature, and soft segments, e.g. polyether, which are above their glass transition temperature and thus flexible at room temperature.

By way of illustration, front sheet 14 may comprise PEBAX 4011, sold by Atochem, which is a block polymer of nylon 6 and polyethylene oxide, an elastomer film which swells at least 30% and preferably 50% of its original dimensions in water, thus allowing more than 260 mg/sq. cm/day rate of water transport.

Other useful materials for forming front sheet 14 will be readily apparent to those skilled in the art in the light of the foregoing description.

The dressing 10 also has a backing sheet 18 covering a back surface of the absorbent layer 12 and secured around the periphery of the dressing 10 to the front sheet 14 in order to protect the layer 12 from contact on the backside of the dressing 10. The backing 18 may comprise the same material as the front sheet 14, if desired. The dressing 10 preferably has a release sheet 20 releasably covering the adhesive 16.

In use, the release sheet 20 is removed from adhesive 16, and the dressing 10 is applied to the skin S surrounding a wound W of the patient. The adhesive 16 is applied in such a manner that pores in the adhesive 16 permit wound fluid to contact exposed areas of the front sheet 14, which serves as a path to the absorbent layer 12.

The PEBAX 4011 sheet 14 is a thermoplastic elastomer in which the nylon crystallites form cross links for the polyethylene oxide flexible matrix. As a thin film, it is elastomeric when dry, but quickly takes up water when exposed to a liquid. In order to apply the adhesive 16 to the front sheet 14, the front sheet 14 is dried very thoroughly, and then the adhesive 16 is bonded to the front sheet 14 by thermobonding.

In an alternative form, the front sheet 14 can be any elastomeric film that will transfer water as a continuous film that can be coated with an adhesive. Other copolymers based on polyethylene oxide soft segments and a variety of hard segment options would be available, for example hard segments could be nylon 12, nylon 11, polyurethane or polyester. Materials of this kind are available for example PEBAX, a trademark of Atochem, nylon polymers, Estane, a trademark of B.F. Goodrich, polyurethane polymers, and Hytrel, a trademark of E.I. DuPont Denemours, polyester polymers. The absorbent layer 12 can be hydrogel with a sufficient capacity for water, which can draw water quickly enough that fluid from the wound or sweat from the skin will be transferred vertically into the gel and not laterally to undermine the skin adhesive. The layer 12 should have sufficient enough capacity so as not to become saturated and lose its drawing power.

The dressing of the present invention maintains a moist wound environment, will also effectively keep wound fluid away from the surrounding skin, and can handle the production of fluids such as water at rates of the order of 3000 mg/72 hrs./sq. cm. In addition, it will be able to transfer sweat produced by the skin glands in a vertical direction, thus preventing undermining of the adhesive. Another advantage is the non-adherent nature of the wound contact surface. Many dressings that absorb wound fluid utilize fabric structures whose fibers can adhere to the wound surface, whereas the present dressing utilizes no fibers.

In addition, since both the front sheet 14 and absorbent layer 12 will swell in the presence of water, they may be utilized to retain water soluble agents for subsequent delivery to the wound. These agents might be anti-microbial agents, water soluble growth factors, or other agents.

The foregoing detailed description is given for clearness of understanding only, and no unnecessary limitations should be understood therefrom, as modifications will be obvious to those skilled in the art.

What is claimed is:

1. A wound dressing adapted to absorb and retain wound fluids, comprising, in order:
   (1) a backing sheet for protecting the backside of said dressing;
   (2) a hydrogel layer adapted to absorb at least two hundred percent of its original weight in water;
   (3) a continuous front sheet covering only the surface of said hydrogel layer opposed from said backing sheet, said front sheet comprising a water-swellable, water-insoluble polymeric material which is characterized as being elastomeric when dry; and
   (4) a porous adhesive layer coated on the free outer surface of said front sheet for adhering said dressing to the skin covering said wound and for permitting passage of fluid from said wound therethrough.

2. A dressing as defined in claim 1 wherein at least one of said hydrogel layer and said front sheet includes a water soluble reagent.

3. A dressing as defined in claim 2 wherein said reagent comprises an anti-microbial agent.

4. A dressing as defined in claim 3 wherein said anti-microbial agent is iodine.

5. A dressing as defined in claim 1 wherein the dressing is capable of handling the production of water at rates of the order of 3000 mg/72 hrs/sq cm.

6. A dressing as defined in claim 1 wherein the front sheet swells at least 30% of its original dimensions in water.

7. A dressing as defined in claim 6 wherein the front sheet allows water transport at a rate of more than 260 mg/sq cm/day.

8. A dressing as defined in claim 1 wherein said polymeric material comprises a block polymer having hard segments and soft segments.

9. A dressing as defined in claim 23 wherein the hard segments are selected from the group consisting of nylon, polyester, polyurethane, polystyrene, and polycarbonate.

10. A dressing as defined in claim 9 wherein the hard segments are glass or crystalline at room temperature.

11. A dressing as defined in claim 8 wherein the soft segments comprise a polyether.

12. A dressing as defined in claim 11 wherein the soft segments are above their glass transition temperature and are flexible at room temperature.

* * * * *